United States Patent [19]
Jada

[11] Patent Number: 5,998,561
[45] Date of Patent: Dec. 7, 1999

[54] CATALYST AND COMPOSITION FOR SILICONE DENTAL IMPRESSION MATERIALS

[75] Inventor: Sivananda S. Jada, Cheshire, Conn.

[73] Assignee: Jeneric/Pentron Incorporated, Wallingford, Conn.

[21] Appl. No.: 09/024,180

[22] Filed: Feb. 17, 1998

Related U.S. Application Data

[60] Provisional application No. 60/040,285, Mar. 11, 1997.

[51] Int. Cl.⁶ .................................................. C08G 77/08
[52] U.S. Cl. ............................................ 528/15; 573/109
[58] Field of Search ................................ 523/109; 528/15

[56] References Cited

U.S. PATENT DOCUMENTS

| | | | |
|---|---|---|---|
| 3,715,334 | 2/1973 | Karstedt | 260/46.5 P |
| 3,775,452 | 11/1973 | Karstedt | 260/429 R |
| 3,814,730 | 6/1974 | Karstedt | 260/46.5 UA |
| 4,020,014 | 4/1977 | Service et al. | 252/511 |
| 4,273,902 | 6/1981 | Tomioka et al. | 525/478 |
| 4,359,565 | 11/1982 | Puppe et al. | 528/15 |
| 4,600,751 | 7/1986 | Lee et al. | 525/404 |
| 4,657,959 | 4/1987 | Bryan et al. | 524/266 |
| 4,782,101 | 11/1988 | Waller et al. | 523/120 |
| 4,806,575 | 2/1989 | Waller et al. | 523/120 |
| 4,957,667 | 9/1990 | Hamer | 264/16 |
| 5,066,714 | 11/1991 | Inoue et al. | 524/731 |
| 5,085,811 | 2/1992 | Hamer | 264/16 |
| 5,086,148 | 2/1992 | Jochum et al. | 528/15 |
| 5,258,435 | 11/1993 | Huggins et al. | 524/357 |
| 5,367,001 | 11/1994 | Itoh et al. | 523/109 |
| 5,596,025 | 1/1997 | Oxman et al. | 523/109 |
| 5,684,060 | 11/1997 | Konings et al. | 523/109 |
| 5,830,951 | 11/1998 | Fiedler | 525/478 |

FOREIGN PATENT DOCUMENTS 0 117 056  8/1984  European Pat. Off. .

OTHER PUBLICATIONS

"Silicones", *Kirk–Othmer Encyclopedia of Chemical Technology*, 3d Ed., vol. 20, pp. 922–962 (1982).

*Primary Examiner*—Margaret G. Moore
*Attorney, Agent, or Firm*—Cantor Colburn LLP

[57] ABSTRACT

A curable silicone dental impression composition is presented, preferably comprising a polyorganohydrogensiloxane having at least one silicon-bonded hydrogen atom; a silicone polymer having at least alkenyl groups; a vinyl siloxane/platinum/palladium catalyst complex; and inorganic fillers and other additives known in the art. The catalyst in accordance with the present invention is a complex of 1,3-divinyltetramethyldisiloxane and hexachloroplatinic acid doped with palladium, and prevents outgassing of hydrogen. The final catalyst complex has a platinum content in the range from about 1.1%–1.2% platinum and 500–600 ppm palladium.

25 Claims, No Drawings

CATALYST AND COMPOSITION FOR SILICONE DENTAL IMPRESSION MATERIALS

CROSS-REFERENCE TO RELATED APPLICATION

This application claims priority to U.S. Provisional Application No. 60/040,285 filed on Mar. 11, 1997.

BACKGROUND OF THE INVENTION

1. Field of the Invention

The present invention relates to a catalyst for use with dental impression compositions for the preparation of the oral tissue models required for the preparation of dental prostheses such as crowns, inlays or dentures. In particular, the invention relates to a catalyst composition comprising a vinyl siloxane/platinum/palladium complex. Such complex is easy to prepare, and minimizes the outgassing that characterizes prior art compositions for forming silicone dental impression materials.

2. Relevant Art

Dental impression materials are used to accurately form an impression of the shape, size, and relative locations of both hard and soft tissues within the mouth. Typically, a gypsum slurry is then used to form a model from the impression. Elastically deformable impression materials are used so that upon removal of the impression from within the mouth, their deformation, if any, is restored to the original form. However, it is equally important that the material resist further deformation or shrinkage, in order to provide an accurate model. Commonly used impression materials include agar, alginates, polysulfide rubbers, polyether rubbers, silicone rubbers, and the like. However, room-temperature vulcanization (RTV) silicone rubbers have become the impression material of choice, as they are essentially tasteless and odorless, cure quickly, and have both excellent elasticity and dimensional stability.

RTV silicone rubber is classified as either condensation or addition type. Each is generally formed from a two component curable silicone prepolymer system, comprising a silicone polymer base with a crosslinking agent and a metal and/or peroxide catalyst. Condensation type silicone rubbers are formed from a curable silicone prepolymer composition comprising a first silicone polymer base component, generally consisting of a hydroxy dimethyl polysiloxane having terminal or pendant hydroxyl groups, and a second component comprising a crosslinking agent generally consisting of a silicic acid ester, for example an alkyl orthosilicate such as tetraethyl orthosilicate, and an organic tin catalyst. However, such a system is disadvantageous in that it still has an offensive odor due to the liquid catalyst, and the elastomer evolves volatile by-products during the condensation reaction, such as alcohols. Furthermore, the presence of unreacted alkyl silicate causes the impression to undergo a gradually increasing dimensional change upon setting due to hydrolysis and post-condensation reactions.

RTV addition-curing silicone rubbers, on the other hand, are formed from a curable silicone prepolymer composition comprising a first silicone polymer base component generally consisting of a hydrogen polymethylsiloxane having at least one terminal or pendant hydrogen, and a second component comprising a vinyl polymethylsiloxane crosslinking agent and a platinum catalyst. These addition-cure silicone rubbers have marked advantages over the prior art silicone impression materials. Such silicone impression materials undergo a linear shrinkage in the order of only about 0.1%, i.e., about one-fourth to one-tenth or less of that of the conventional silicone impression materials twenty-four hours after the impression has been taken. Accordingly, it is possible to prepare a model having a high dimensional accuracy. The prepolymer composition is tasteless and odorless, and furthermore can be mixed and kneaded in equal amounts as the silicone components have approximately the same viscosity. Addition-cure silicone rubbers therefore have excellent dental performance and workability.

However, the liberation of small quantities of hydrogen gas from RTV addition cured polyvinylsiloxane elastomers, due to the platinum-catalyzed addition reaction between the silicone hydrogen bond and an unsaturated carbon-carbon bond, is a recognized problem. The evolution of the hydrogen gas results in the formation of pores in the stone cast formed from the impression, producing an undesirable pitted surface. A number of attempts have been made to suppress or otherwise minimize pore formation.

U.S. Pat. No. 4,273,902 to Tomioka discloses using 0.5 ppm or more of finely divided palladium and/or a finely divided palladium alloy containing 10% by weight or more of palladium, without inhibiting the addition reaction. Various other elemental metals are also cited, including platinum, but are stated to be inferior to palladium and fail to eliminate the undesirable pores in the surface of the resulting model. As shown below, addition of palladium metal is in fact ineffective for preventing formation of all bubbles.

In an attempt to overcome the drawbacks of Tomioka, U.S. Pat. No. 5,684,060 to Konings et al. discloses addition of inorganic, organic, or organometallic compounds of palladium to the prepolymer system in order to prevent outgassing. While apparently more effective than palladium metal, the palladium compounds are still in addition to the platinum complexes used to catalyze the addition reaction.

Other attempts to control outgassing include coating the formed dental impression with a finely divided palladium before pouring the gypsum, as described in U.S. Pat. No. 4,957,667 to Hamer. U.S. Pat. No. 5,086,148 to Jochum further discloses the addition of metal powders or metal-coated silica or calcium carbonate to absorb hydrogen in polyether-type RTV addition-cure impression compositions, which may not be applicable to silicone compositions. Use of palladium metal-containing zeolites is disclosed in U.S. Pat. No. 4,359,565 to Puppe.

None of these applications discloses an effective catalyst further useful for the prevention of outgassing. Accordingly, there remains a need for catalysts for silicone dental impression materials that are active, and help prevent outgassing during the hydrosilylation reaction.

SUMMARY OF THE INVENTION

The above-discussed and other drawbacks and deficiencies of the prior art are overcome or alleviated by the catalyst of the present invention, comprising an unsaturated aliphatic siloxane/platinum/palladium complex. The complex is formed by the complexation of hexachloroplatinic acid doped with palladium and an organosilicon derivative having at least two unsaturated groups, for example 1,3-divinyltetramethyldisiloxane. Preferably, the complex in accordance with the present invention comprises from about 1.1% to 1.2% by weight platinum and 500–600 ppm palladium. Use of the catalyst to form RTV addition-type silicone rubber compositions results in materials with good properties and few or no observable bubbles.

Preferably, the curable silicone dental impression prepolymer composition in accordance with the present invention comprises:

(a) a polyorganohydrogensiloxane having at least one silicon-bonded hydrogen atom;

(b) a silicone polymer having at least two alkenyl groups;

(c) the above-described catalyst; and (d) inorganic fillers and other additives known in the art.

In another embodiment, the present invention comprises a molded hydrophilic silicone article prepared by shaping and curing the above-described composition. Such articles include dental impressions, lithographic plates, release liners, reflective sheeting, adhesives, coatings and sealants.

In yet a further embodiment, the present invention provides a method for making a dental impression, comprising the step of making a negative model of teeth and/or hard tissue using the above-described catalyst and composition.

DETAILED DESCRIPTION OF THE INVENTION

The catalyst in accordance with the present invention is a vinyl disilane or disiloxane platinum palladium complex. Platinum-only complexes of this type are known in the art as "Karstedt" type catalysts, and are described, for example, in U.S. Pat. Nos. 3,715,334, 3,775,452, and 3,814,730, the disclosures of which are incorporated by reference herein.

The complex of the present invention is formed by the reaction of a silane or siloxane having at least two unsaturated groups with hexachloroplatinic acid doped with palladium. The silane or siloxane has at least two aliphatic unsaturated groups and optionally at least one lower alkyl, cycloalkyl, lower haloalkyl, lower alkoxy, or phenyl group. Suitable aliphatic unsaturated groups include, but are not limited to, vinyl, allyl, cycloalkenyl (for example cyclohexenyl), ethynyl, 2-propynyl, and the like. Suitable lower alkyl groups include but are not limited to methyl, ethyl, propyl, butyl and like; suitable lower haloalkyl groups include but are not limited to chloromethyl and dichloroethyl and the like; suitable alkoxy groups include but are not limited methoxy, ethoxy, propoxy, and the like; and suitable phenyl groups may be unsubstituted or substituted with lower alkyl or lower alkoxy groups. A preferred siloxane is 1,3-divinyltetramethyldisiloxane. A suitable silane includes but is not limited to tetravinylsilane or divinylmethoxysilane.

Hexachloroplatinic acid ($H_2PtCl_6 \cdot xH_2O$) preparations doped with palladium are available from DeGussa Corporation, South Plainfield, N.J. The hexachloroplatinic acid preparation preferably comprises from about 30% to about 50% platinum by weight. The hexachloroplatinic acid preparation further comprises from about 0.0001% to about 75% palladium by weight, and preferably from about 4% to about 20% palladium by weight. Most preferably, the hexachloroplatinic acid preparation comprises about 35% to about 39% platinum by weight and about 4% to about 15%, even more preferably about 10% palladium by weight.

Preferably, the complex is formed under a partial vacuum or under an inert gas by means well-known in the art. Thus, the hexachloroplatinic acid preparation is first complexed with a silane or siloxane having at least two unsaturated groups, such as 1,3-divinyltetramethyldisiloxane, $H_2C=CH-Si(CH_3)_2-O-Si(CH_3)_2-CH=CH_2$, in the presence of sodium bicarbonate, followed by azeotropic distillation with isopropyl alcohol. The resulting product is then further complexed and diluted with a vinylpolydimethylsiloxane. Such vinylpolydimethylsiloxane may be "V-200", a 200 cps vinylpolydimethylsiloxane having a vinyl content of 0.683%, available from OSI Specialties. Other high vinyl content/low viscosity vinylpolydimethylsiloxanes may also be used, such as VS-50 from OSI Specialties. The final product is isolated by filtration. The complex is neutralized and filtered to provide a catalyst that is about 0.5% to about 4% by weight platinum and from about 250 to about 1000 ppm by weight palladium. Preferably, the catalyst complex comprises about 0.9% to about 4%, and even more preferably about 1.1% to about 1.2% platinum by weight and 400–600 ppm palladium by weight.

The fundamental components of the prepolymer composition according to the present invention comprise:

(a) a polyorganohydrogensiloxane having at least one silicon-bonded hydrogen atom;

(b) a silicone polymer having at least two alkenyl groups;

(c) the above-described catalyst; and (d) inorganic fillers and other additives known in the art.

So long as the components a, b, c, and d are separated into two parts, one comprising a and the other c, the respective components b and d may be incorporated into either or both of the components a and c. Alternatively, the components b and d may be mixed together as a third component. It should be noted that, if the impression composition is capable of being cured by mixing the two components a and c therewith, then all available mixing methods are used for this purpose. Suitable silicone prepolymer compositions are well-known in the art and are described, for example, in "Silicones", *Kirk-Othmer Encyclopedia of Chemical Technology*, 3d Ed., 20, 922–962 (1982), the disclosure of which is incorporated herein by reference.

The organohydrogen polysiloxane serving as component b may be that having in its molecule hydrogen atoms bonded to at least two silicone atoms. Such compounds are known and include siloxane copolymers having different polymerization degrees and both terminals closed by trialkylsilyl or dialkylhydrogensilyl radicals.

Of the composition according to the present invention, the organopolysiloxane having vinyl groups which serves as the crosslinking component may be any known organopolysiloxane having in its molecule at least two vinyl groups, such as that having vinyl terminated triorganosiloxyl groups or having terminal groups closed by hydroxyl groups and a skeleton comprising a $(CH_3)(CH_2=CH)SiO$ unit and a $R_2SiO$ unit (wherein R denotes a monovalent saturated hydrocarbon radical such as methyl, ethyl, butyl and phenyl radicals).

The dental impression compositions of the present invention may additionally comprise inorganic fillers, including but not limited to those known in the art such as diatomaceous earth, calcium carbonate, silicic acid, calcium sulfate, zirconium silicate, amorphous and crystalline silica, zirconium oxide, titanium oxide and aluminum oxide. Surface-treated fillers may also be used, such surface treatments including silanization and the like.

Other additives which may be used in the present invention include polymerization inhibitors, colorants, perfumes, fluidity regulators, reinforcing agents, plasticizers, and the like.

Typically, the compositions according to the present invention are packaged, stored, and used in the conventional manner for curable silicone prepolymer systems. Thus, the two components are generally stored separately, the first component comprising the silicone polymer base component, fillers and other adjuvants; and the second component comprising the cross-linking agent and catalyst. A polysiloxane surfactant polymer may be present in either component, or both. However, where the catalyst may react with constituents of either component, then it should be added only to the non-reactive component.

The present invention is further illustrated by the following non-limiting examples.

General Procedures

Dental impression compositions were prepared by mixing the base polymer components ("component A") and catalyst polymer components ("component B") (equal parts by weight) in a kneader. All parts and percentages are by weight unless otherwise indicated.

In all examples, Component A was prepared by mixing 78 parts of polydimethylsiloxane containing terminal vinyl groups with a mixture of fluids having the viscosity of 1,000,000 or over 65,000 and 1,000 mPa.s at 25° C., 5.5 parts of polydimethylsiloxane containing hydrosilyl groups, and 16.5 parts of a combination of silanized inorganic filler(s), surfactant, processing aid, and colored pigments.

Component B was prepared by mixing 76 parts of polydimethylsiloxane similar to that used in Component A, 2 parts catalyst, 0.1 parts of polymerization inhibitor, and 21.8 parts of a combination of inorganic filler(s) and processing aid.

Preparation of Catalyst

The divinylsiloxane/platinum/palladium catalyst in accordance with the present invention may be synthesized by swirling together 249 mL isopropyl alcohol, 10 g hexachloroplatinic acid doped with 10.27% palladium (DeGussa Corporation), 29.9 g sodium bicarbonate, and 31.10 g 1,3-divinyltetramethyldisiloxane. The flask is then attached to a rotary evaporator and mixed for 30 minutes in a water bath maintained at 50° C. Vacuum is then applied to remove approximately 33 mL of isopropyl alcohol/water/HCl as its azeotrope. A further 33 mL of isopropyl alcohol is twice added and removed under reduced pressure as an azeotrope. V-200 (OSI Specialities), 0.55 lbs., is added to the reaction flask, and the flask rotated for 3–3½ hours in a water bath held at 50° C. Vacuum is then applied to remove as much isopropyl alcohol/water/HCl as possible, followed by addition and azeotropic removal of 33 mL of isopropyl alcohol (three times). The remaining reaction mixture is then filtered through a Büchner funnel under vacuum to remove residual sodium bicarbonate. The filtrate is collected. Analysis for platinum and palladium content indicates that the catalyst comprises 1.09% platinum and 0.051–0.052% (510–520 ppm) palladium by weight.

Comparison of Catalyst Preparations

Addition-cure silicone dental impression materials were prepared using three different catalysts: a vinylsiloxane/platinum complex, a vinylsiloxane/platinum complex with added palladium, and the vinylsiloxane/platinum/palladium complex in accordance with the present invention. The vinylsiloxane/platinum complex was prepared in the same manner as that described for the vinylsiloxane/platinum/palladium complex, except that the hexachloroplatinic acid was not doped with palladium. The vinylsiloxane/platinum complex with added palladium was prepared by simply adding an amount of palladium to the vinylsiloxane/platinum complex that would result in the same level of palladium as that found in the vinylsiloxane/platinum/palladium complex in accordance with the present invention. Five samples of each impression material were formed, and the physical characteristics of the samples were measured and averaged as summarized in the Table:

| Characteristic | | Vinylsiloxane/ Pt complex | Vinylsiloxane/ Pt/Pd complex | Vinylsiloxane/Pt complex, added Pd |
|---|---|---|---|---|
| Work time (min.) | | 2:00 | 2:30 | 2:15 |
| Oral set time (min.) | | 4:50 | 4:30 | 4:40 |
| Set on pad (min.) | | 12:00 | 11:45 | 11:00 |
| Shore 'A' | 10 min. | soft | soft | 20 |
| hardness | 20 min. | 25 | 25 | 45 |
| | 30 min. | 45 | 45 | 45 |
| | 45 min. | 45 | 45 | 45 |
| Outgassing* | | medium-sized bubbles on gypsum | no bubbles; very smooth surface | smaller sized bubbles |
| Ultimate | Mean | 154.19 | 175.236 | 148.928 |
| tensile | St. Dev. | 9.919 | 17.486 | 18.075 |
| strength (psi) | % C.V. | 6.433 | 9.979 | 12.137 |
| Yield | Mean | 127.881 | 143.895 | 123.077 |
| strength | St. Dev. | 8.801 | 16.445 | 15.633 |
| (psi) | % C.V. | 6.882 | 11.429 | 12.702 |
| Yield | Mean | 376.076 | 451.468 | 459.567 |
| Elongation | St. Dev. | 45.912 | 82.33 | 62.116 |
| (psi) | % C.V. | 12.208 | 18.236 | 13.516 |
| Break | Mean | 129.254 | 156.477 | 101.573 |
| Strength | St. Dev. | 22.002 | 19.469 | 51.125 |
| (psi) | % C.V. | 17.022 | 12.442 | 50.333 |
| Break | Mean | 298.019 | 354.272 | 355.109 |
| Elongation | St. Dev. | 43.263 | 59.352 | 50.378 |
| (psi) | % C.V. | 14.517 | 16.753 | 14.187 |
| Modulus | Mean | 35.672 | 33.958 | 27.38 |
| (psi) | St. Dev. | 3.058 | 3.489 | 1.479 |
| | % C.V. | 8.573 | 10.275 | 5.401 |

*Observed thirty minutes after the start of the mixture of Components A and B.

As can be seen by inspection of the data, the catalyst in accordance with the present invention provides acceptable work and set times compared to conventional platinum complex catalysts. Importantly, no bubbles are evolved during the gypsum casting process. The catalyst complex of the present invention is also superior to compositions which merely contain added palladium. Ultimate tensile strength, yield strength, and break strength of the finished composition are superior to finished compositions using other catalysts. Yield elongation, break elongation, and modules are either superior or similar compositions using other catalysts.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A room temperature curable dental silicone composition for the manufacture of a dental impression material comprising a mixture of
    (a) a polyorganohydrogensiloxane having at least one silicone-bonded hydrogen atom;
    (b) a silicone polymer having at least two alkenyl groups; and
    (c) an unsaturated aliphatic silane/platinum/palladium catalyst complex or an unsaturated aliphatic siloxane/platinum/palladium catalyst complex.

2. The room curable composition in accordance with claim 1, wherein
    the catalyst complex is formed by the complexation of a hexachloroplatinic acid preparation doped with palladium with a silane or siloxane having at least two aliphatic dienes.

3. The room curable composition of claim 2, wherein
    the complexation is with 1,3-divinyltetramethyldisiloxane.

4. The room curable composition in accordance with claim 2, wherein
   the hexachloroplatinic acid preparation comprises from about 30% to about 50% by weight platinum and from about 0.0001% to about 75% by weight palladium.
5. The room curable composition in accordance with claim 2, wherein
   the hexachloroplatinic acid preparation comprises from about 4% to about 20% by weight palladium.
6. The room curable composition in accordance with claim 2, wherein
   the hexachloroplatinic acid preparation comprises from about 35% to about 39% by weight platinum and from about 4% to about 15% by weight palladium.
7. The room curable composition in accordance with claim 1, wherein
   the catalyst complex comprises from about 0.5% to about 4% by weight platinum and from about 250 to about 1000 ppm by weight palladium.
8. The room curable composition in accordance with claim 1, wherein
   the catalyst complex comprises from about 0.9% to about 4% by weight platinum and from about 400–600 ppm by weight palladium.
9. A cured dental silicone composition, formed by curing a mixture of
   (a) a polyorganohydrogensiloxane having at least one silicon-bonded hydrogen atom;
   (b) a silicone polymer having at least two alkenyl groups; and
   (c) an unsaturated aliphatic silane/platinum/palladium catalyst complex or an unsaturated aliphatic siloxane/platinum/palladium catalyst complex.
10. The room curable composition in accordance with claim 9, wherein
    the catalyst complex is formed by the complexation of a hexachloroplatinic acid preparation doped with palladium with a silane or siloxane having at least two unsaturated groups.
11. The room curable composition in accordance with claim 10, wherein
    the complexation is with 1,3-divinyltetramethyldisiloxane.
12. The room curable composition in accordance with claim 10, wherein
    the hexachloroplatinic acid preparation comprises from about 30% to about 50% by weight platinum and from about 0.0001% to about 75% by weight palladium.
13. The room curable composition in accordance with claim 10, wherein
    the hexachloroplatinic acid preparation comprises from about 4% to about 20% by weight palladium.
14. The room curable composition in accordance with claim 10, wherein
    the hexachloroplatinic acid preparation comprises from about 35% to about 39% by weight platinum and from about 4% to about 15% by weight palladium.
15. The room curable composition in accordance with claim 9, wherein
    the catalyst complex comprises from about 0.5% to about 4% by weight platinum and from about 250 to about 1000 ppm by weight palladium.
16. The room curable composition in accordance with claim 9, wherein
    the catalyst complex comprises from about 0.9% to about 4% by weight platinum and from about 500–600 ppm by weight palladium.
17. The cured composition in accordance with claim 9, in the form of a dental impression comprising a negative mold of oral tissue.
18. A method of making a dental silicone impression, comprising making a negative mold of oral tissue, using as said mold a curable silicone composition comprising a mixture of
    (a) a polyorganohydrogensiloxane having at least one silicon-bonded hydrogen atom;
    (b) a silicone polymer having at least two alkenyl groups; and
    (c) an unsaturated aliphatic silane/platinum/palladium catalyst complex or an unsaturated aliphatic siloxane/platinum/palladium catalyst complex.
19. The room curable composition in accordance with claim 18, wherein
    the catalyst complex is formed by the complexation of a hexachloroplatinic acid preparation doped with palladium with a silane or siloxane having at least two unsaturated groups.
20. The room curable composition in accordance with claim 19, wherein
    the complexation is with 1,3-divinyltetramethyldisiloxane.
21. The room curable composition in accordance with claim 19, wherein
    the hexachloroplatinic acid preparation comprises from about 30% to about 50% by weight platinum and from about 0.0001% to about 75% by weight palladium.
22. The room curable composition in accordance with claim 19, wherein
    the hexachloroplatinic acid preparation comprises from about 4% to about 20% by weight palladium.
23. The room curable composition in accordance with claim 19, wherein
    the hexachloroplatinic acid preparation comprises from about 35% to about 39% by weight platinum and from about 4% to about 15% by weight palladium.
24. The room curable composition in accordance with claim 18, wherein
    the catalyst complex comprises from about 0.5% to about 4% by weight platinum and from about 250 to about 1000 ppm by weight palladium.
25. The room curable composition in accordance with claim 18, wherein
    the catalyst complex comprises from about 0.9% to about 4% by weight platinum and from about 500–600 ppm by weight palladium.

* * * * *